(12) United States Patent
Niazi

(10) Patent No.: US 8,852,435 B2
(45) Date of Patent: Oct. 7, 2014

(54) PURIFICATION AND SEPARATION TREATMENT ASSEMBLY (PASTA) FOR BIOLOGICAL PRODUCTS

(75) Inventor: Sarfaraz Niazi, Deerfield, IL (US)

(73) Assignee: Therapeutics Proteins International, LLC, Chicago, IL (US)

( * ) Notice: Subject to any disclaimer, the term of this patent is extended or adjusted under 35 U.S.C. 154(b) by 517 days.

(21) Appl. No.: 13/286,193

(22) Filed: Nov. 29, 2011

(65) Prior Publication Data

US 2012/0142047 A1    Jun. 7, 2012

(51) Int. Cl.
*B01D 15/08* (2006.01)
*B01D 15/22* (2006.01)
*C12M 1/12* (2006.01)
*C07K 1/16* (2006.01)
*C07K 1/22* (2006.01)

(52) U.S. Cl.
CPC . *B01D 15/22* (2013.01); *C07K 1/16* (2013.01); *C07K 1/22* (2013.01)
USPC ............. 210/638; 210/656; 210/660; 435/41; 435/69.3; 435/70.1; 435/70.3; 435/293.1; 435/307.1; 435/308.1; 530/412; 530/413; 530/417

(58) Field of Classification Search
CPC ........ B01D 15/08; B01D 15/22; B01D 15/36; B01D 15/361; B01D 15/362; B01D 15/363; B01D 15/3804; B01D 15/3809; B01D 15/3828; C07K 1/16; C07K 1/22; B65B 1/04
USPC ........... 210/198.2, 263, 266, 282, 502.1, 635, 210/638, 656, 660, 675, 690; 435/41, 63, 435/69.3, 69.4, 69.51, 69.6, 69.7, 71.1, 435/89.1, 287.7, 288.6, 3, 7.1, 308.1, 70.1, 435/70.3, 289.1, 293.1; 422/69, 70, 427, 422/534; 436/177, 178, 518, 528, 543; 530/412, 413, 417
See application file for complete search history.

(56) References Cited

U.S. PATENT DOCUMENTS

| | | | | |
|---|---|---|---|---|
| 3,615,222 A | * | 10/1971 | Mead | 436/500 |
| 3,768,979 A | * | 10/1973 | Mead et al. | 422/430 |
| 4,816,161 A | * | 3/1989 | Olness et al. | 210/638 |
| 4,879,030 A | * | 11/1989 | Stache | 210/238 |
| 4,976,866 A | * | 12/1990 | Grinstead et al. | 210/638 |
| 5,698,004 A | | 12/1997 | Hartmann | |
| 5,855,789 A | | 1/1999 | Smith et al. | |
| 6,265,224 B1 | * | 7/2001 | Collis et al. | 436/178 |

(Continued)

FOREIGN PATENT DOCUMENTS

| | | |
|---|---|---|
| EP | 0247821 A2 | 12/1987 |
| WO | 2011009623 A1 | 1/2011 |

OTHER PUBLICATIONS

International Search Report and Written Opinion for PCT/US12/60398, dated Apr. 5, 2013.

*Primary Examiner* — Joseph Drodge
(74) *Attorney, Agent, or Firm* — Sarfaraz K. Niazi; Cheryl Liljestrand

(57) ABSTRACT

An assembly capable of capturing and purifying expressed biological products during or at the end of a bioreaction cycle is disclosed wherein a binding resin is kept separated from the contents of the bioreactor allowing capturing, harvesting and purification of biological products in a bioreactor; the invention additionally provides means of removing undesirable metabolic products as well as provides for efficient loading of chromatography columns.

19 Claims, 1 Drawing Sheet

(56) References Cited

U.S. PATENT DOCUMENTS

| | | |
|---|---|---|
| 6,610,528 B1 | 8/2003 | Mathur et al. |
| 7,306,934 B2* | 12/2007 | Arora et al. .................. 435/180 |
| 7,311,880 B2* | 12/2007 | Perman et al. ................. 422/69 |
| 8,506,797 B2* | 8/2013 | Niazi ............................ 210/85 |
| 8,668,886 B2* | 3/2014 | Niazi ............................ 422/603 |
| 2005/0186177 A1 | 8/2005 | Michael et al. |
| 2005/0238641 A1 | 10/2005 | Burton et al. |
| 2006/0266684 A1 | 11/2006 | Pichl |
| 2008/0017569 A1 | 1/2008 | Ramsey et al. |
| 2008/0022630 A1 | 1/2008 | Fuss et al. |
| 2008/0255027 A1* | 10/2008 | Moya et al. ....................... 514/2 |
| 2009/0014389 A1 | 1/2009 | Noyes et al. |
| 2009/0188211 A1* | 7/2009 | Galliher et al. ................ 53/434 |
| 2010/0310548 A1* | 12/2010 | Yeh et al. ................... 424/130.1 |
| 2011/0198286 A1* | 8/2011 | Niazi ............................ 210/638 |
| 2013/0017577 A1* | 1/2013 | Arunakumari et al. ...... 435/71.1 |
| 2013/0177919 A1* | 7/2013 | Kaufmann et al. ......... 435/6.13 |

* cited by examiner

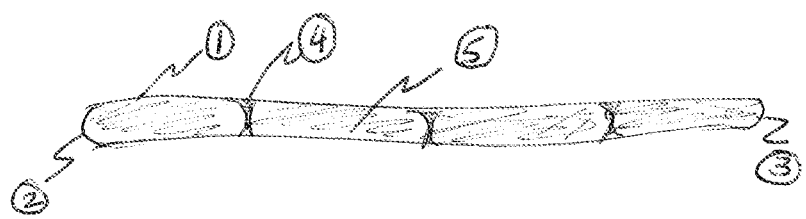

PURIFICATION AND SEPARATION TREATMENT ASSEMBLY (PASTA) FOR BIOLOGICAL PRODUCTS

BACKGROUND OF THE INVENTION

Bioreactors are used to grow mammalian cell culture in which the cells produce an extracellular component, such as an antibody or recombinant protein. Bioreactors are also used for virus production. A separation process is performed in order to concentrate and purify the desired component from the bioreactor, which may, for example, be useful as a therapeutic or diagnostic agent. Bioreactors are complex mechanical devices that provide mainly the mixing and gasification of liquids to grow a target biological culture; this step is followed by several additional unit processes including the separation of cells, filtration to reduce the volume of nutrient medium, loading onto chromatography columns and several steps of purification. In recent years, there has been a raised awareness to produce many target biological products on a short turn around time, particularly as it relates to the products needed to combat terrorism-related needs; this also includes the need to quickly develop and manufacture vaccines and antibodies.

Current methods require large capital investment and lengthy and tedious processes to manufacture these products. There is a great unmet need for creating a manufacturing method to produce target biological products to reduce the manufacturing steps and reduce the cost of drug manufacturing and discovery.

A system that combines all steps in the manufacturing of target biological products, from growing cells to secrete them to separating the target biological product and purifying it within the same container that remains closed during the entire operation will change the way target biological drugs are developed and manufactured. This will be most suitable for situations where a product needs to be manufactured quickly such as in counter-terrorism operations as well as when protecting the public from epidemics since this system will allow a quick deployment of the manufacturing.

The aspect about combining the separation and purification of drugs within the bioreactor is novel and a disruptive technology. While the bioreactors are exclusively used for the purpose of growing cells, their role can be expanded to include other processes that can be completed within the bioreactor.

There is an unmet need to develop a manufacturing method for expressing and separating a target biological product from other components in the nutrient medium, combining the steps of expressing and separating within the bioreactor by binding the target biological product with a resin within a bioreactor, discarding the nutrient medium and eluting the target biological product as a concentrated solution; this will eliminate at least three steps in the separation and purification of target biological products—filtration or centrifugation to remove cell culture, perform ultrafiltration for volume reduction, and purification of target biological product by selective elution from the bioreactor; the last use makes the bioreactor a chromatography column.

Other unattended problems in the manufacture of biological drugs is in the need to remove undesirable metabolites from a bioreactor to enhance the growth of cell culture; a method for removing these components will improve the yield of production.

Another unattended problem in the manufacture of biological drugs is in the purification step wherein a binding resin is loaded on to a chromatography column and is often wasted in the process of loading. There is a need to device an assembly that would totally contain the binding resin in a sheath that is disposed in a chromatography column reducing the losses incurred in the loading.

BRIEF SUMMARY OF THE INVENTION

The present invention provides in one aspect a method for preparing a variety of target biological products. The method comprises expressing the target biological product in a traditional manner in a bioreactor and then adding a resin to the bioreactor to capture the target biological product either during the expression phase or at the end of the expression cycle. The resin is contained in a flexible tube that can be removed from the bioreactor and disposed in a chromatography column. Alternately, where the method involves first completing the expression of the target biological product, the flexible tube is allowed to stay in the bioreactor and various buffers used to elute a pure form of target biological product directly from the bioreactor.

The present invention also teaches a method of recharging the resin used and thus allows repeated use of resin reducing the overall cost of manufacturing of target biological products.

Capturing the target biological products and possibly the metabolites formed during the bioreaction process is often useful when the target biological product is toxic to the recombinant cells or where higher concentration of target biological product in the bioreactor adversely affects the productivity of the expression process.

Also provided in this invention are the techniques for removing undesirable metabolites in a bioreaction cycle and the methods for loading a resin in a chromatography column.

BRIEF DESCRIPTION OF THE DRAWINGS

FIG. 1 is a side sectional view of the claimed invention.

DETAILED DESCRIPTION OF THE INVENTION

In one aspect, the present invention provides a purification and separation treatment assembly (PASTA) for the target biological products and metabolites of bioreaction in a bioreactor such that the resin capturing these component is kept separated from the contents of the bioreactor to allow separation of the resin from the contents of the bioreactor.

In another aspect, the present invention provides an assembly containing a resin wherein the long length of the assembly (because of its smaller diameter) allows for efficient contacting of the resin inside the PASTA with the expressed products in the bioreactor. The PASTA can be of variable size and sized by simply cutting off an appropriate length and also reconnecting various lengths simply by heat sealing. By securing the resin in a mesh housing, the loss of resin is reduced in its handling as well. The PASTA comprising a porous tube has opening designed to retain the resin inside the housing; an optimal opening of the mesh will be about 50μ as most of the resins used have an average diameter size larger than 50μ; however, in those instances where a finer resin is used, the mesh size of the housing is reduced accordingly. It is noteworthy that to allow fast equilibration of resin, a maximum exposure to the nutrient media is required therefore choosing the maximum size of mesh that will retain the resin is desirable. In most instances, the flexible tube housing will be a nylon mesh tube of a diameter less than 5 mm. The PASTA will be assembled to various lengths, ranging from a few centimeters to hundreds of meters and the mesh housing sealed at fixed intervals of about 50 to 100 mm; this fixed interval sealing is necessary to keep the resin from segregating within the housing and thus reducing the contact with the nutrient media in the bioreactor. This sealing is readily achieved by using sealing bars operating on heat or induction method, the latter being the preferred method.

It is also recommended that prior to using the PASTA, it is washed in water to remove any smaller particles of resins and other debris that may have been produced in the assembly of PASTA. Where PASTA is used during a bioreaction process, as suggested below, the PASTA is sterilized preferably by gamma radiation; otherwise, it is used in a pharmaceutically clean state to avoid contaminating the target product. Where PASTA is removed during a process, it is advisable to leave one end of PASTA outside the bioreactor to allow it to be removed by pulling out of the bioreactor. Alternately, a string can be attached to PASTA; however, as the PASTA is a narrow tube, the resin unexposed when one end of PASTA is left outside of bioreactor is minimal and it forms a better practice. Where a longer or shorter length of PASTA is desired it can be readily made by simply cutting off the flexible tube without the need to seal the ends since the housing is periodically sealed; it will only incur the loss of resin contained in the compartment that is cut; this resin can be collected and used later to minimize losses. Similarly, when a longer length is desired, it can be assembled by connected various shorter length housings by heat sealing them together. It is envisioned that in a commercial production environment, the PASTA will be kept rolled in a reel and when needed, pulled out and cut to length as desired. The PASTA reel can be kept in a liquid that prevents contamination of resin and washed prior to introducing it in the bioreactor.

In yet another aspect, the present invention provides a method for manufacturing purified target biological products in the bioreactor either by using the PASTA at the end of the expression cycle or by periodically removing the expressed target biological product from the bioreactor and then subjecting it to purification outside the bioreactor.

Turning initially to FIG. 1, a side sectional view of a preferred embodiment of the PASTA comprising a flexible porous tube 1 holding a resin 5 with sealed ends 2 and 3 as well as sealing at pre-determined distances 4 along the length of the tube.

Two distinct types of manufacturing methods are envisioned using the claimed PASTA in the present invention. First, the PASTA is disposed inside a bioreactor upon the completion of the steps of expression of target biological product. At this point, the target biological product has been fully expressed and is present as a solution in the nutrient media used for the expression of the target biological product in the bioreactor. The PASTA of the present invention comprises a tube that contains a suitable quantity of a resin, which is capable of binding the target biological product present in the solution state in the bioreactor. The quantity of resin used is determined by first determining the concentration of the target biological product in the bioreactor and then by the theoretical binding capacity of the resin. For example, monoclonal antibodies and fusion proteins are bound about 30-50 mg/mL of Protein A resin; so for a 1000 L batch wherein the expression level is about 1 G/L (e.g., for the fusion protein etanercept or the monoclonal antibody rituximab). Thus to bind 1000 G of the protein, the quantity of resin needed is about 20 to 33 Liters. The cost of this quantity of resin is about $300,000 to $500,000. This is a large amount but given that the Protein A resin can be used over again for hundreds of times, overall cost of process is not high. The length of the PASTA used will depend on the diameter and the density of resin in the PASTA. For example, 20 L of resin will be contained in about 250 meters of PASTA of about 5 mm in diameter and about 65 meters of a 10 mm diameter PASTA. It is understood that for 1000 L batch, the size of bioreactor is about 2,000 L and thus addition of a volume of 20-33 L will not affect the overall volume inside the bioreactor. After adding the PASTA, the bioreactor is operated in a mixing mode with continued gasification since it is often seen that stopping the gasification causes degradation of protein. The nutrient media is tested frequently, generally based on pre-determined times from pilot studies. When the concentration of etanercept or rituximab in the bioreactor is reduced to less than 1 mg/L or another such end point, the process of capturing the target biological product is considered complete. At this point the manufacturer is offered several choice for purification of these proteins. The ideal solution is to use the bioreactor as a purification chromatography column. This is readily achieved by first draining out the nutrient media (about 1000 L in the above example) along with suspended cells (most likely Chinese Hamster Ovary cells). A bioreactor will likely have a drain port, and if not, one can be created to accommodate making this special use of the bioreactor. This step has instantly obviated one of the most expensive step in protein purification—removal of cells and volume reduction of nutrient media and a saving of about 48 hours of processing time in the specific example given above. The equipment cost saving alone will be into millions of dollars at this stage. Now the proteins of interest are present in a bound form with Protein A resin used and contained inside the device. At this point, the bioreactor drain can be closed and the bioreactor filled with sufficient liquid to cover the PASTA that will have been settled at the bottom of the bioreactor. This liquid (most likely water) will be of a pH and conductivity that it will not allow breakdown of the binding of etanercept or rituximab from Protein A. The purpose of adding a liquid at this stage is to remove any adherent cells or other particle debris that may have remained within the PASTA. After allowing sufficient time to mix, the liquid is drained in a manner similar to how the nutrient media was removed in an earlier step. Now the bioreactor can be filled to submerge the PASTA with a buffer that will causing breakdown of binding of substances bound to Protein A other than the proteins of choice [a better choice is to select a buffer that would just begin to break down the binding of target proteins but only to an insignificant level]. This buffer is drained after mixing for a pre-determined time. At this stage, the final step of purification can be started wherein a buffer of pH and electrolyte concentration that will breakdown the binding completely [ideally less than 100%] and after mixing this buffer is collected as a concentrated solution of purified target protein such as etanercept or rituximab. The three steps described can be combined to give two steps based on prior pilot studies. The method of manufacturing of target proteins like etanercept and rituximab described above is an efficient process that will save very large cost of manufacturing of all types of target biological drugs. Just eliminating the cost of downstream processing in traditional equipment, the manufacturer will save millions of dollars in equipment cost, cost of equipment validation, long times of processing and the inevitable degradation and yield losses which are common in every downstream process. The present invention has now provided a game-changing solution to the manufacturing of target biological drugs that can be readily afforded by companies and institutions on a smaller budget for the manufacturing of these target biological products and also allow a faster development of drugs.

The method for manufacturing a target biological product described above presented a preferred embodiment of the invention. However, the capital cost of the operation described above can be significantly reduced by a modification of the present invention. Let us assume that the manufacturer is able to afford only one-tenth the cost of the resin Protein A used in the above exercise; in this case, the method would be modified such that 5% of the required resin in the PASTA is added at one time and when it equilibrates with the nutrient media binding 5% of the target protein, the PASTA is removed and immediately replaced with fresh PASTA (PASTA that has been subjected to a buffer to remove binding of the target protein) representing 5% of the resin. The removed PASTA is then taken to another container wherein it is submerged in a buffer solution to perform cleansing and purification as described above. At this point, the PASTA is ready to be re-used in the bioreactor; keeping two sets of PASTA each with 5% resin allows a continuous process of purification and whereas it will take longer time, this will certainly reduce the initial capital cost of operations. It is noteworthy that in many instances, the cost of resin is not as high as noted for Protein A and in some instances the resins can even be discarded after single use. However, the present invention offers the manufacturer a choice of methods based on the affordability of the process.

There are numerous other areas of improvement of the manufacturing of target biological products, two of which are readily addressed by the present invention. In instance, the present invention is used to remove undesirable metabolites to improve the expression of target proteins and in another the disclosed invention is used to load a downstream chromatography column to reduce the losses that generally occur in the loading of columns used lose resin.

The preferred embodiment described above pertained to an example where the target biological expression process is first brought to an end; however, there remain many other processes where it is critical to continuously remove the expressed target biological either because of its toxicity to the expression engine comprising cells or where the product is unstable or even where a higher concentration of the product reduces the productivity of cells expressing the target biological product. Currently, the only option available in the art is to filter out the nutrient media (to leave the producing cells in the bioreactor) and replace it with fresh media; this removes the target biological product from the bioreactor. The removal of nutrient media requires extensive filtration processes that exposed the target biological product to contamination and require extreme care and manipulation of the process, making it an extremely expensive exercise. The present invention offers an ideal solution to removing the target biological product from the bioreactor on an ongoing basis. This is achieved by disposing the PASTA containing a desirable resin either periodically or continuously; either from the beginning of the process or starting at a specific stage of the expression of target biological drugs. The PASTA is allowed to equilibrate in the bioreactor and them removed from the bioreactor and replaced with fresh PASTA. The PASTA removed may then be subjected to a similar treatment as described in the first embodiment for cleansing and purification and the PASTA re-used, minimizing the cost of resin used in the process. Once the target protein is removed, the nutrient media may be replenished with nutrient elements. In an ideal embodiment, the manufacturer will be able to devise a composition of resin that will also remove any metabolites from the nutrient media in the event where accumulation of these is detrimental to the efficiency of expression. The PASTA can be made using resins that specifically bind the metabolites separate from the PASTA intended to capture the target biological product, in such instances, a plurality of PASTA can be used.

The preferred embodiments disclosed above merely describe a limited number of applications of the present invention. Those who are familiar with the art of manufacturing target biological products will find many other uses of the invention and these are all included here by reference.

COMMON EMBODIMENTS

In a first embodiment, the present invention proposes a method for manufacturing purified form of target biological drugs within a bioreactor by capturing the expressed target biological product in a PASTA holding a resin capable of binding the target biological product.

In a second embodiment, the present invention proposes a method for manufacturing for purifying a target biological product using the bioreactor as a traditional chromatography column, from where the target biological product is eluted using various buffers.

In a third embodiment, the present invention proposes a method for enhancing the yield of target biological product expressed in a bioreactor by allowing periodic removal of the target biological product as it is being expressed.

In a fourth embodiment, the present invention proposes a method for separating the target biological product form the nutrient medium and the target biological culture within the bioreactor eliminating the need for the centrifugation of the nutrient medium to remove the target biological culture and filtration of the nutrient medium to reduce its volume.

In a fifth embodiment, the present invention proposes a method of purifying a target biological product in a bioreactor wherein selectively binding the target biological product to a resin and the eluting it gradually performs the same function that is normally performed in chromatography column. Thus, in such instance, the bioreactor acts like a chromatography column.

In an sixth embodiment, the present invention provides a means of substantially reducing the cost of recombinant drug manufacturing by eliminating some of the most costly and time consuming steps.

In a seventh embodiment, the present invention provides a means of manufacturing toxic target biological substances that can harm the cell culture producing them.

In an eight embodiment, the present invention provides a means of enhancing the yield of production by removing the expressed target biological product continuously from the bioreactor.

In a ninth embodiment, the present invention provides a means of using a small amount of capture resin by recycling the PASTA containing the resin reducing the cost of biological product purification substantially.

In a tenth embodiment, the present invention provides an alternate to perfusion method of producing biological products; instead of replacing nutrient media, the present invention can be used to remove undesirable metabolites and when using the PASTA for this purpose, replenishing the nutrient media with fresh nutrition and components lost to PASTA. This application reduces the risk of contaminating the bioreactor, reduces the cost and enhances the production yield.

In a tenth embodiment, the present invention provides a method for removing undesirable metabolites in a bioreaction to improve the productivity of the cell culture used and this is accomplished by introducing the PASTA during a bioreaction cycle and once the undesired metabolites are removed, recovering the PASTA and re-using it.

In an eleventh embodiment, the present invention provides and efficient method of loading a chromatography column for purification by winding the PASTA in a reel to a height equal to the diameter of the chromatography column. As the height of the reel is kept equal to the height of the column, a snug fit is achieved. Perforations in the side plates of a reel allow free movement of eluting solvents. This prevents significant losses of resin during the purification process.

PRIOR ART

The instant invention is intended to convert bioreactors into a type of separative bioreactors. In the past substantial progress has been made in membrane bioreactors (MBR) that had the ability to separate the products within the bioreactors. The MBR process was introduced by the late 1960s, as soon as commercial scale ultrafiltration (UF) and microfiltration (MF) membranes were available. The original process was introduced by Dorr-Olivier Inc. and combined the use of an activated sludge bioreactor with a cross-flow membrane filtration loop. The flat sheet membranes used in this process were polymeric and featured pore sizes ranging from 0.003 to 0.01 µm. Although the idea of replacing the settling tank of the conventional activated sludge process was attractive, it was difficult to justify the use of such a process because of the high cost of membranes, low economic value of the product (tertiary effluent) and the potential rapid loss of performance due to membrane fouling. As a result, the focus was on the attainment of high fluxes, and it was therefore necessary to pump the mixed liquor suspended solids (MLSS) at high cross-flow velocity at significant energy penalty (of the order 10 kWh/m3 product) to reduce fouling. Due to the poor economics of the first generation MBRs, they only found applications in niche areas with special needs like isolated trailer parks or ski resorts for example.

The breakthrough for the MBR came in 1989 with the idea of Yamamoto and co-workers to submerge the membranes in the bioreactor. Until then, MBRs were designed with the separation device located external to the reactor (side-stream MBR) and relied on high transmembrane pressure (TMP) to maintain filtration. With the membrane directly immersed into the bioreactor, submerged MBR systems are usually preferred to sidestream configuration, especially for domestic wastewater treatment. The submerged configuration relies on coarse bubble aeration to produce mixing and limit fouling. The energy demand of the submerged system can be up to 2 orders of magnitude lower than that of the sidestream systems and submerged systems operate at a lower flux, demanding more membrane area. In submerged configurations, aeration is considered as one of the major parameter on process performances both hydraulic and biological. Aeration maintains solids in suspension, scours the membrane surface and provides oxygen to the biomass, leading to a better biodegradability and cell synthesis.

The other key steps in the recent MBR development were the acceptance of modest fluxes (25% or less of those in the first generation), and the idea to use two-phase bubbly flow to control fouling. The lower operating cost obtained with the submerged configuration along with the steady decrease in the membrane cost encouraged an exponential increase in MBR plant installations from the mid 90s. Since then, further improvements in the MBR design and operation have been introduced and incorporated into larger plants. While early MBRs were operated at solid retention times (SRT) as high as 100 days with mixed liquor suspended solids up to 30 g/L, the recent trend is to apply lower solid retention times (around 10-20 days), resulting in more manageable mixed liquor suspended solids (MLSS) levels (10-15 g/L). Thanks to these new operating conditions, the oxygen transfer and the pumping cost in the MBR have tended to decrease and overall maintenance has been simplified. There is now a range of MBR systems commercially available, most of which use submerged membranes although some external modules are available; these external systems also use two-phase flow for fouling control. Typical hydraulic retention times (HRT) range between 3 and 10 hours. In terms of membrane configurations, mainly hollow fiber and flat sheet membranes are applied for MBR applications.

Despite the more favorable energy usage of submerged membranes, there continued to be a market for the side stream configuration, particularly in industrial applications. For ease of maintenance the side stream configuration can be installed at low level in a plant building. Membrane replacement can be undertaken without specialist equipment, and intensive cleaning of individual banks can be undertaken during normal operation of the other banks and without removing the membranes modules from the installation.

As a result research continued with the side stream configuration, during which time it was found that full-scale plants could be operated with higher fluxes. This has culminated in recent years with the development of low energy systems which incorporate more sophisticated control of the operating parameters coupled with periodic back washes, which enable sustainable operation at energy usage as low as 0.3 kWh/m3 product.

Argonne scientists (www.anl.gov) recently used electrical force to transport organic acids away from the biocatalyst across an ion-exchange membrane and into a concentrate chamber, very similar to normal metabolism processes for handling acids. To provide the electricity in a cost efficient fashion, researchers turned to electrodeionization (EDI). EDI is an established commercial technology for producing high-purity water. Previously, Argonne scientists modified EDI so that it could be used for desalination of chemical and agricultural products. To accomplish this, researchers molded loose ion exchange resin beads into a porous resin wafer, enabling the capture of charge salts and acids at dilution levels with high-energy efficiency and significantly reduced waste streams compared to conventional processing. This became the basis for the Argonne's separative bioreactor. Researchers also realized that although direct enzyme immobilization on membranes provided excellent product separations, insufficient enzyme density limited the overall performance. In order to increase the density, the scientists integrated enzyme immobilization technology into the porous resin wafer and created a material that can efficiently produce and remove organic acids. As Argonne designed its separative bioreactor, researchers incorporated enzyme capture resin beads into the resin wafer. Sugars were converted by the immobilized biocatalyst to the target acids, and the product was electrically transported into a concentrate channel. This resulted in reactions occurring without buffering or neutralization. Argonne's immobilization technology also allows in-situ stripping and replacement of degraded enzymes without disassembling the system.

However, every type of membrane separative bioreactor disclosed utilized a similar principle of forcing a target biological product across a membrane. The instant invention differs significantly by providing a PASTA capable of containing a resin capable of binding the target biological product, the membrane holding the resin has no specific function except to keep the resin separated form the bulk liquid in the bioreactors and also to prevent larger scale organisms or cells to contact the resin. The separation function in the instant invention is provided by a non-specific, non-electrically driven reaction.

The prior art on the design and operation of separative bioreactors is silent on the concept of instant invention. The main references to separative bioreactors of use in target biological sciences appear as U.S. patent application Ser. No. 10/993,642 file 19 Nov. 2004 wherein a separative bioreactor is disclosed. Accordingly, it is a separative bioreactor, comprising an anode and a cathode, a plurality of reaction chambers each having an inlet and an outlet and each including a porous solid ion exchange wafer having ion-exchange resins, each of the reaction chambers being interleaved between a cation exchange membrane and an anion exchange membrane or between either a cation or an anion exchange membrane and a bipolar exchange membrane, a plurality of product chambers each having an inlet and an outlet and separated from one of the reaction chambers by either a cation or an anion exchange membrane, recirculation mechanism for transporting material between the reaction chamber inlets and outlets and for transporting product between the product chamber inlets and outlets, and mechanism for supplying an electric potential between the anode and the cathode causing ions to be transported between chambers, whereby counterions retained or produced in each of the reaction chambers during the production of an ionizable organic product including product ions combine with oppositely charged ions to form molecules some or all of which are transported to reaction chamber inlets while product ions are transported into an adjacent product chamber to combine with oppositely charged ions to form product in a product stream exiting the product chamber outlets continuously recirculate to the product chamber inlets to increase the concentration of product in the product stream. None of the features described in this application are material to the instant invention and none of the essential features of the instant inventions are disclosed in this application.

The U.S. patent application Ser. No. 11/732,992 filed 5 Apr. 2007 discloses a porous solid ion exchange wafer comprising a combination of an biomolecule: capture-resin and an ion-exchange resin forming a charged capture resin containing a transition metal anion of +2 valence within said wafer. Additionally, this application claims a separative bioreactor, comprising an anode and a cathode, a plurality of reaction chambers at least some being formed from a porous solid ion exchange wafers having a combination of an biomolecule capture-resin and an ion-exchange resin forming a charged capture resin within said wafer and having a genetically tagged biomolecule immobilized on said charged capture resin, each of said porous solid ion exchange wafers having a charged capture resin therewithin being interleaved between a cation exchange membrane and an anion exchange membrane, and mechanism for supplying an electric potential between the anode and the cathode. None of these disclosures are common to the instant invention and the essential features of the instant invention are not recited in this application.

The U.S. Pat. No. 7,306,934 issued 11 Dec. 2007 discloses a porous solid ion exchange wafer for immobilizing biomolecules, said wafer comprising a combination of an biomolecule capture-resin containing a transition metal cation of +2 valence and an ion-exchange resin. The patent further discloses a separative bioreactor, comprising an anode and a cathode, a plurality of reaction chambers at least some being formed from a porous solid ion exchange wafers having a combination of art biomolecule capture-resin and an ion-exchange resin and having a genetically engineered tagged biomolecule immobilized on said biomolecule capture resin, each of said porous solid ion exchange wafers being interleaved between a cation exchange membrane and an anion exchange membrane, and mechanism for supplying an electric potential between the anode and the cathode. The instant invention does not rely on any features disclosed in this patent, nor any features of the instant invention are recited in this patent.

The U.S. Pat. No. 7,799,548 issued 21 Sep. 2011 is for a method of in situ stripping a genetically tagged biomolecule from a porous solid ion exchange wafer in a bioreactor, the wafer having a combination of a biomolecule capture-resin and an ion-exchange resin forming a charged capture resin within the wafer and having a genetically tagged biomolecule immobilized on said biomolecule capture-resin, comprising contacting the porous solid ion exchange wafer in the bioreactor with a stripping fluid at a temperature and for a time sufficient to strip at least some of the genetically tagged biomolecule therefrom. This patent additionally claims method of in situ stripping a genetically tagged biomolecule from a porous solid ion exchange wafer in a bioreactor and thereafter regenerating a genetically tagged biomolecule onto the porous solid ion exchange wafer, the wafer having a combination of a biomolecule capture-resin and an ion-exchange resin forming a charged capture resin within the wafer and having a genetically tagged biomolecule immobilized on said biomolecule capture-resin thereon, comprising contacting the porous solid ion exchange wafer in the bioreactor with a stripping fluid at a temperature and for a time sufficient to strip at least some of the genetically tagged biomolecules therefrom, and thereafter contacting the stripped porous solid ion exchange wafer in the bioreactor with an effective amount of a genetically tagged biomolecules at a temperature and for a time sufficient to immobilize genetically tagged biomolecules on the charged capture resin. The instant invention does not rely on any disclosures made in this patent nor are any of the essential features of the instant invention disclosed in this patent.

The U.S. Pat. No. 7,141,154 issued 28 Nov. 2006 discloses a method of continuously making an organic ester from a lower alcohol and an organic acid, comprising, introducing an organic acid or an organic salt into and/or producing an organic acid or an organic salt in an electrodeionization (EDI) stack having an anode and a cathode and a plurality of reaction chambers each formed from a porous solid ion exchange resin wafer interleaved between anion exchange membranes or an anion exchange membrane and a cation exchange membrane or an anion exchange membrane and a bipolar exchange membrane, providing mechanism for establishing an electric potential between the EDI anode and cathode, wherein at least some reaction chambers are esterification chambers and/or bioreactor chambers and/or chambers containing an organic acid or salt, whereby an organic acid or organic salt present in the EDI stack disassociates into a cation and an anion with the anion migrating into an associated esterification chamber through an anion exchange membrane if required and reacting with a lower alcohol in the esterification chamber to form an organic ester and water with at least some of the water splitting into a proton and a hydroxyl anion with at least some of the hydroxyl anion migrating to an adjacent chamber, said migration of ions being facilitated by establishing an electric potential across the EDI anode and cathode. The patent additionally discloses an apparatus for manufacturing an organic ester, comprising an electrodeionization (EDI) stack having an anode and a cathode and a plurality of reaction chambers each formed from a porous solid ion exchange resin wafer interleaved between anion exchange membranes or an anion exchange membrane and either a cation exchange membrane or a bipolar membrane, mechanism for establishing an electrical potential between said EDI anode and said cathode, at least some of said reaction chambers being esterification chambers or esterification chambers separated from an adjacent bioreactor chamber by an anion exchange membrane and/or an acid/base capture chamber, said bioreactor chambers each containing an ion exchange resin wafer capable of forming an organic acid or salt from an ionizable fluid flowing therein, said esterification chambers each containing an ion exchange resin wafer capable of forming an organic ester and water from a lower alcohol and an anion of an organic acid or salt, a source of anions supplied directly to said esterification chambers or supplied from adjacent chambers, and a supply of lower alcohol to said esterification chambers, whereby when a potential is established across said EDI anode and cathode at least some hydroxyl anions in said esterification chambers from water splitting migrate across said anion exchange membranes to adjacent chambers to drive the reaction to continuously produce an organic ester. None of the features disclosed in this patent are material to the instant invention and none of the essential features of the instant invention are disclosed or taught in this patent.

In summary, the prior art disclosed above teaches the use of porous solid ion exchange wafer for immobilizing biomolecules, said wafer comprising a combination of an biomolecule capture-resin containing a transition metal cation of +2 valence; it also teaches a separative bioreactor, comprising an anode and a cathode, a plurality of reaction chambers at least some being formed from a porous solid ion exchange wafers (above) having a combination of art biomolecule capture-resin and an ion-exchange resin and having a genetically engineered tagged biomolecule immobilized on said biomolecule capture resin, each of said porous solid ion exchange wafers being interleaved between a cation exchange membrane and an anion exchange membrane, and mechanism for supplying an electric potential between the anode and the cathode. The instant invention is significantly different from the separative bioreactor taught above. First, the instant invention does not require use of electrodes, or resins with a transition cation of +2 valence or immobilized metal ion affinity chromatography. The use of EDI (electrodeionization) and specific use of tags and limited nature of solvents to remove the captured target biological products mainly enzymes makes this patent teachings distinctly different from the instant invention. In addition, and most significantly, the prior art cannot be used with the preferred embodiment of the instant invention wherein flexible bioreactors are taught.

Moreover, the prior art requires additional hardware that adds substantial cost to the processing of manufacturing target biological products while the instant invention combines several processes into one without adding any new cost element. The prior art is also specific to certain types of molecules while the instant invention is generic to every type of target biological product.

REFERENCES

Ahmad A, Pereira E O, Conley A J, Richman A S, Menassa R., Green biofactories: recombinant protein production in plants. Recent Pat Biotechnol. 2010 November; 4 (3):242-59.

Atkinson, S., Research studies predict strong growth for MBR markets. Membrane Technology (2006) 8-10

Bazinet L., Electrodialytic phenomena and their applications in the dairy industry: a review. Crit Rev Food Sci Nutr. 2005; 45 (4):307-26.

Cui, Z F, Chang, V, Fane, A G., The use of gas bubbling to enhance membrane process, J. Memb. Sci. 2211 (2003) 1-35

Drews, A, Evenblij, H, Rosenberger, S., Potential and drawbacks of microbiology-membrane interaction in membrane bioreactors, Environmental Progress 24 (4) (2005) 426-433

Ghosh A C, Bora M M, Dutta N N., Kadouri A., Developments in liquid membrane separation of beta-lactam antibiotics. Adv Biochem Eng Biotechnol. 1991; 44:27-64.

Hubbuch J, Thömmes J, Kula M R., Biochemical engineering aspects of expanded bed adsorption. Biotechnol Adv. 2004 July; 22 (6):433-44.

Kraume, M, Bracklow, U, Vocks, M, Drews, A., Nutrients Removal in MBRs for Municipal Wastewater Treatment. Wat. Sci. Tech. 51 (2005), 391-402

Le-Clech, P, Chen, V, Fane, A G., Fouling in membrane bioreactors used for wastewater treatment—A review. J. Memb. Sci. 284 (2006) 17-53.

Shirgaonkar I Z, Lanthier S, Kamen A., Acoustic cell filter: a proven cell retention technology for perfusion of animal cell cultures. J Gen Appl Microbiol. 2003 August; 49 (4):219-33.

Shukla A A, Thömmes J., Recent advances in large-scale production of monoclonal antibodies and related proteins. Trends Biotechnol. 2010 May; 28 (5):253-61.

Singh, S M, Panda A K, Judd, S., Solubilization and refolding of bacterial inclusion body proteins. J. Biosciences and Bioengineering, 99:4, 303-310, 2005

Stephenson, T, Judd, S, Jefferson, B, Brindle, K., Membrane bioreactors for wastewater treatment, IWA Publishing (2000)

The MBR book (2006) Principles and applications of membrane bioreactors in water and wastewater treatment, Elsevier, Oxford Toda K., Theoretical and methodological studies of continuous microbial bioreactors. Biotechnol Bioeng. 2003 Jun. 30; 82 (7):751-65.

Voisard D, Meuwly F, Ruffieux P A, Baer G, Potential of cell retention techniques for large-scale high-density perfusion culture of suspended mammalian cells. Bioseparation. 1996 April; 6 (2):91-105.

Wu M, Wu R, Zhang Z, Zou H., Preparation and application of organic-silica hybrid monolithic capillary columns. Electrophoresis. 2011 January; 32 (1):105-15.

I claim:

1. A method for harvesting and purifying a target biological product at the end of a production cycle comprising:
    a) Expressing a target biological product in a bioreactor;
    b) Disposing in the bioreactor at the end of the production cycle, an appropriate length of a purification and separation treatment assembly (PASTA) comprising: a flexible porous tube filled with a binding resin, wherein the porous tube comprises a plurality of pores smaller in size than the size of the binding resin and wherein the porous tube is sealed at both ends to provide a pre-determined quantity of resin;
    c) Capturing the target biological product by mixing the contents of the bioreactor to allow substantially complete binding of the target biological product to the resin in the PASTA;
    d) Removing the contents of the bioreactor except the PASTA from the bioreactor;
    e) Eluting the target biological product from the PASTA held in the bioreactor by adding to the bioreactor a buffer capable of removing the binding of the target biological product from the resin in the PASTA.

2. The method according to claim 1, wherein the flexible porous tube is made of plastic, nylon and a composite material.

3. The method according to claim 1, wherein the diameter of the flexible porous tube is less than 10 mm.

4. The method according to claim 1, wherein the size of the pores ranges from 1 micron to 50 microns.

5. The method according to claim 1, wherein the resin comprises an ionic-exchange resin, a hydrophobic resin, an affinity resin or a mixture thereof.

6. The method according to claim 1, wherein the resin comprises a protein or a peptide as a ligand.

7. The method according to claim 1, wherein the resin comprises a resin with specific affinity towards the target biological product.

8. The method according to claim 1, wherein the resin comprises a plurality of resins.

9. The method for harvesting and purifying a target biological product according to claim 1, wherein the step (e) is repeated using different buffers.

10. The method for harvesting and purifying a target biological product according to claim 1, wherein the PASTA is removed from the bioreactor after step (d) and packed in a chromatography column for purification.

11. A method for harvesting a target biological product during its production comprising:
    a) Starting an expression cycle of the target biological product in a bioreactor;
    b) Disposing in the bioreactor a purification and separation treatment assembly (PASTA) comprising: a flexible porous tube filled with a binding resin, wherein the porous tube comprises a plurality of pores smaller in size than the size of the binding resin and wherein the porous tube is sealed at both ends to provide a pre-determined quantity of resin at a pre-determined stage in the expression cycle and leaving one end of the PASTA accessible from the outside of the bioreactor;
    c) Allowing the resin in the PASTA to bind a pre-determined quantity of the target biological product;
    d) Removing the PASTA from the bioreactor by pulling on the end of PASTA accessible from the outside of the bioreactor and replacing it with fresh PASTA;
    e) Submerging the removed PASTA in a separate container holding a buffer capable of breaking the binding of the target biological product with the resin, removing the PASTA from the container to obtain a concentrated solution of purified target protein;
    f) Reusing the PASTA from step (e) in step (b).

12. The method for harvesting a target biological product according to claim 11, wherein the bioreactor is replenished with nutrient elements that are removed by the PASTA.

13. The method for harvesting and purifying a target biological product according to claim 1 or 11, wherein the target biological product is produced by an organism selected from the group consisting of bacteria, yeast, hybrodomas, baculoviruses, mammalian cells or plant cells.

14. The method for harvesting and purification of a target biological product according to claim 1 or 11, wherein the target biological product is selected from the group consisting of a solubilized inclusion body, small protein, enamel matrix protein, fusion protein, tag protein, hormone, parathyroid hormone, growth hormone, gonadotropin, insulin, ACTH, prolactin, placental lactogen, melanocyte stimulating hormone, thyrotropin, calcitonin, enkephalin, angiotensin, cytokines human serum albumin, bovine serum albumin, ovalbumin, glucose isomerase, α-amylase, endo-β, glucanase, growth hormone (GH), IGF-1, IGF-2, PTH, $PGE_2$, TGF-β, TGF-α, bEGF, EGF, PDGF-AB, PDGF-BB, osteoprotegerin (OPG), osteopontin (OP), FGF-1, FGF-2, thyroid hormone, BMP-2, BMP-3, BMP-4, BMP-6, BMP-7, VEGF, L25(OH)$_2$, vitamin $D_3$, caclitonin, IFN-alpha, IFN-beta, IFN-gamma, OCN (osteocalcin), ON (osteonectin), OP-1 (osteogenic protein-1), NGF, collagen, fibronectin, fibrinogen, thrombin, factor XIII, a recombinant protein, a recombinant antibody and a recombinant peptide.

15. A method for removing undesirable metabolites in a production cycle of a target biological product comprising:
    a) Adding to a bioreactor a sufficient quantity of a purification and separation treatment assembly (PASTA) comprising: a flexible porous tube filled with a binding resin or a mixture of binding resins capable of binding one or more undesirable metabolic products in the bioreactor, wherein the porous tube comprises a plurality of pores smaller in size than the size of the binding resin and wherein the porous tube is sealed at both ends;
    b) Removing the PASTA from the bioreactor upon achieving a desired low level of undesirable metabolic products in the bioreactor;
    c) Reacting the removed PASTA with a buffer capable of removing undesirable metabolic products and re-using the PASTA in step (a).

16. The method for harvesting a target biological product according to claim 15, wherein a plurality of PASTA is used to remove any undesirable metabolic products of the production cycle separately from the target biological product.

17. A method for harvesting and purifying a target biological product comprising:
    a) Disposing in the bioreactor at the beginning or during the bioreaction cycle, an appropriate length of a purification and separation treatment assembly (PASTA) comprising: a flexible porous tube filled with a binding resin; wherein the porous tube comprises a plurality of pores smaller in size than the size of the binding resin; and wherein the porous tube is sealed at both ends; to provide a pre-determined quantity of resin;
    b) Expressing the target biological product in a bioreactor;
    c) Allowing the resin in the PASTA to bind a pre-determined quantity of the target biological product;
    d) Removing the contents of the bioreactor except the PASTA from the bioreactor; and
    e) Eluting the target biological product from the PASTA held in the bioreactor by:
        1) adding to the bioreactor a buffer capable of removing the binding of the target biological product from the resin in the PASTA; or
        2) removing the PASTA from the bioreactor and submerging the removed PASTA in a separate container holding a buffer capable of breaking the binding of the target biological product with the resin and removing the PASTA from the container to obtain a concentrated solution of purified target protein.

18. The method of any one of claims 1, 11, 15, or 17, wherein the porous tube is further sealed along the porous tube into regularly spaced segments.

19. The method according to claim 18, wherein the segments range in size from 10 mm to 100 mm.

* * * * *